United States Patent
Pai et al.

(10) Patent No.: US 7,138,387 B2
(45) Date of Patent: Nov. 21, 2006

(54) CLEAR AQUEOUS COMPOSITION COMPRISING PROPOFOL AND HYDROXYPROPYL-BETA-CYCLODEXTRIN

(75) Inventors: Srikanth Annappa Pai, Maharashtra (IN); Sangeeta Hanurmesh Rivankar, Maharashtra (IN); Shilpa Sudhakar Kocharekar, Maharashtra (IN)

(73) Assignee: Bharat Serums and Vaccines Limited, Mumbai (IN)

( * ) Notice: Subject to any disclaimer, the term of this patent is extended or adjusted under 35 U.S.C. 154(b) by 398 days.

(21) Appl. No.: 10/296,765

(22) PCT Filed: Dec. 14, 2000

(86) PCT No.: PCT/IN00/00124

§ 371 (c)(1),
(2), (4) Date: Aug. 18, 2003

(87) PCT Pub. No.: WO01/97796

PCT Pub. Date: Dec. 27, 2001

(65) Prior Publication Data

US 2004/0014718 A1    Jan. 22, 2004

(30) Foreign Application Priority Data

Jun. 21, 2000  (IN)  .................. 573/MUM/2000

(51) Int. Cl.
*A61K 31/724* (2006.01)
*A61K 31/05* (2006.01)

(52) U.S. Cl. ........................ 514/58; 514/731

(58) Field of Classification Search .................. 514/58, 514/731
See application file for complete search history.

(56) References Cited

FOREIGN PATENT DOCUMENTS

WO    WO 96/32135    * 10/1996

OTHER PUBLICATIONS

Trapani, G. et al "Inclusion Complexation of Propofol . . . " J. Pharm. Sci. (1998) vol. 87, No. 4, pp. 514-518.*
MacKenzie, C. "Formulation and evaluation of a propanidid . . . " Int. J. Pharm. (1997) vol. 159, pp. 191-196.*

* cited by examiner

*Primary Examiner*—Leigh C. Maier
(74) *Attorney, Agent, or Firm*—Thorpe North & Western

(57) ABSTRACT

Sterile pharmaceutical stable autoclaved clear aqueous compositions of propofol (2,6-Diisopropyl phenol) suitable for parenteral administration are described. The compositions essentially consist of a complex of propofol with 2-hydroxypropyl-β-cyclodextrin in a weight ratio of 1:30–1:60. This complex of propofol with 2-hydroxypropyl-β-cyclodextrin produces a clear aqueous composition that is stable to autoclaving. The composition is effective as an anaesthetic agent. The process of making these synergistic compositions has been described.

30 Claims, No Drawings

CLEAR AQUEOUS COMPOSITION COMPRISING PROPOFOL AND HYDROXYPROPYL-BETA-CYCLODEXTRIN

FIELD OF THE INVENTION

This invention relates to a pharmaceutical composition of propofol, (2,6-diisopropyl phenol) for parenteral administration. This invention is particularly related to the compositions in which propofol is complexed with 2-hydroxypropyl-β-cyclodextrin (referred to hereinafter as "HPBCD"). This invention is more particularly related to a clear aqueous composition of the propofol—HPBCD complex that is stable to autoclaving and the process to prepare the same.

BACKGROUND OF THE INVENTION

Propofol is an intravenous anesthetic agent characterised by a short recovery time. It has the desirable property of rapid onset and offset of the anaesthetic effect following intravenous administration and minimal accumulation on long-term administration.

Propofol even though is a preferred anesthetic agent, has posed a big challenge to the formulator since its invention because of its aqueous insolubility. It was at first formulated as a 1% aqueous solution containing nonionic surfactant Cremophor EL as a solubiliser. However, Cremophor EL has been implicated in some adverse reactions when administered intravenously, including anaphylactoid reactions.

Subsequently, the anaesthetic agent was formulated as oil-in-water emulsion containing 1% w/v propofol with 10% w/v soybean oil & 1.2% w/v purified egg phosphatide. Lipid based emulsions suffer from several limitations such as poor physical stability, the potential for embolism, pain on injection and increased fat load. Furthermore, strict aseptic techniques must be maintained when handling these formulations since they contain no antimicrobial preservatives and therefore can support rapid growth of microogranisms.

G. Trapani et al (J.P.S. April 1998, 87(4), 514–518) have studied the physicochemical and anaesthetic properties of a freeze dried inclusion complex of propofol with 2-hydroxypropyl-β-cyclodextrin in 1:1 mol/mol (1:8 wt./wt) stoichiometry. In this process, complex formation was achieved after continued stirring for five days.

Pharmaceutical compositions comprising inclusion complex of propofol and 2-hydroxypropyl-β-cyclodextrin have been described in a WO 96/32135. At the ratio of propofol to 2-hydroxypropyl-β-cyclodextrin 1:1.5 to 1:<2 mol/mol (1:11.79 to 1:<15.72 wt./wt.), additional co-solvent was necessary to formulate a clear colourless solution. At 1:2 to 1:2.5 mol/mol stoichiometry (1:15.72 to 1:19.65 wt./wt.) solution was clear. However we find that such solutions are not stable to autoclaving.

Preferred process of sterilisation specified in pharmacopoeias is autoclaving of the product in the final container. Further as propofol is commonly administered by intravenous route to induce and maintain general anaesthesia, terminal sterilisation is the only preferred alternative which offers higher confidence of sterility compliance.

Our main objective of this invention is thus to develop a clear aqueous composition of propofol complexed with HPBCD that is stable to autoclaving thereby making it suitable for parenteral administration in human beings and other mammals.

SUMMARY OF THE INVENTION

Accordingly, the present invention relates to an autoclaved stable clear aqueous pharmaceutical composition of propofol, suitable for parenteral administration comprising propofol and 2-hydroxypropyl-β-cyclodextrin (HPBCD) in a wt. ratio of propofol: HPBCD from about 1:30 to about 1:60.

The composition of the present invention further comprises other conventional additives as required by parenteral dosage form.

The present invention further relates to a process for preparing an autoclaved stable clear aqueous pharmaceutical composition of propofol, suitable for parenteral administration comprising steps of i) addition of propofol as such or in a solution form to solution of 2-hydroxypropyl-β-cyclodextrin (HPBCD) either in water or other solvents in a wt. ratio of propofol: HPBCD from about 1:30 to about 1:60 under stirring;

ii) keeping said solution of propofol and HPBCD under intimate contact till complexation of propofol with HPBCD is complete to obtain a clear bulk solution;

iii) removing the said solvent if other than water and adding water;

iv) making up the volume with water to a required concentration of propofol in said composition obtained at the end of step (iii);

v) filtering the said composition obtained at the end of step (iv) through 2µ to 0.2µ filter;

vi) filling the said filtrate obtained at the end of step (v) in containers such as vials, ampoules, followed by nitrogen purging and sealing the filled containers;

vii) autoclaving the sealed containers filled with said filtrate.

The present invention also relates to an autoclaved stable clear aqueous pharmaceutical composition of propofol, suitable for parenteral administration as described herein and made by the process of the present invention as described above.

DETAILED DESCRIPTION OF EMBODIMENTS OF THE INVENTION

The different embodiments of the invention described below are applicable to the product to the process of making the product and for the product made by the process. The propofol content of the composition of this process of invention is from about 1 mg/ml to about 20 mg/ml, preferably from about 2 mg/ml to about 10 mg/ml, more preferably about 10 mg/ml and about 2 mg/ml. The 10 mg/ml composition is suitable as bolus injection and requires to be diluted if used for continuous infusion. However, 2 mg/ml composition is suitable for continuous infusion and requires no dilution before administration.

The preferred wt./wt. ratio of propofol to HPBCD is from about 1:30 to about 1:45. The more preferred wt./wt. ratio is about 1:30.

The conventional additives which may be used in the process of this invention contain commonly used additives such as anticrystallising agents, antioxidants, buffers and isotonic diluents, which in the usual quantities added do not affect to the clarity and stability of the composition.

Anticrystallising agents are selected from a group of pharmaceutically acceptable compounds such as Glycerin, Propylene glycol, Polyethylene glycol of low molecular weight series. Preferably the anticrystallising agent used is Glycerin.

Antioxidants are selected from a group of pharmaceutically acceptable compounds such as Ethylene diamine tetraacetic acid and salts thereof Sodium metabisulphite, Acetylcysteine, Ascorbic acid. Preferably the antioxidant used is Disodium edetate Buffers are selected from a group of pharmaceutically acceptable buffer systems such as Phosphate buffer, Citrate buffer, Glycine buffer containing any of the commonly used compounds or a mixture of compounds such as Citric acid, Sodium citrate, Potassium citrate, Glycine, Phosphoric acid, Sodium phosphate, Disodium hydrogen phosphate, Sodium dihydrogen phosphate, Potassium phosphate, Dipotassium hydrogen phosphate, Potassium dihydrogen phosphate, Sodium hydroxide, Potassium hydroxide, Hydrochloric acid. Preferably the buffer used is a mixture of Potassium dihydrogen phosphate and Sodium hydroxide.

Isotonic diluents are selected from a group of pharmaceutically acceptable diluents such as Dextrose solution and Sodium chloride solution. Preferably the isotonic diluent used is Dextrose solution.

In this process of invention, propofol is added as such for complexation with HPBCD solution or it is added as a solution in pharmaceutically acceptable organic solvent(s) and the solvent is removed from the system after the complexation is complete. Organic solvents are selected from a group of solvents such as Ethanol, Methanol and Isopropyl alcohol or a mixture thereof Preferably the organic solvent used is Ethanol.

HPBCD is dissolved in water for complexing with propofol. Alternatively HPBCD is dissolved in pharmaceutically acceptable organic solvents and the solvent is removed from the system after the complexation is complete. Organic solvents used are Ethanol, Methanol or a mixture thereof Preferably the organic solvent used is Ethanol.

In the process of present invention, complexation of propofol with HPBCD is brought about by intimate contact of these two ingredients. The complexation of propofol with HPBCD is carried out at a temperature of about 10° C. to about 50° C., preferably at ambient temperature.

In the process of present invention there are four modes of adding propofol to HPBCD solution;

| | Propofol | HPBCD |
|---|---|---|
| 1) | As such | Solution in water |
| 2) | Solution in organic solvent | Solution in water |
| 3) | As such | Solution in organic solvent |
| 4) | Solution in organic solvent | Solution in organic solvent |

In the first mode of addition, since propofol is not soluble in water, the intimate contact is brought about by mixing using conventional stirrers. Faster complexation is achieved when high shear mixer, colloid mill or high pressure homogeniser is used for bringing about intimate contact.

In second, third and fourth mode of addition, the organic solvent is removed totally under vacuum preferably at the temperature of less than 50° C.

In the third and fourth mode of addition, the residue obtained after total removal of organic solvent is dissolved in water or water containing additives.

The compositions prepared by the process of the present invention are specifically clear aqueous solutions prepared under controlled conditions as required for parenteral dosage form.

The process of the present invention gives a clear aqueous composition of propofol, which is advantageous in terms of no added fat load, no adverse reactions of emboli, no pain on injection, improved stability and a scope for visual inspection before administration in view of its clarity.

The process of the present invention also offers the advantage of terminal sterilisation in the final container which is the preferred process specified in pharmacopoeias. Further as the process of the present invention gives a composition of propofol that is commonly administered by intravenous route, the terminal sterilisation is the only preferred alternative which offers higher confidence of sterility compliance. Terminal sterilisation offers further advantage of parametric release, that is the release of the batch of sterilised products based on process data rather than on the basis of submitting a sample of the items to sterility testing.

The process of the present invention gives a composition that is suitable as a ready marketable product. Acute toxicity study in mice carried out on samples after storing for 18 months at 2° C.–8° C. along with freshly prepared products indicated no change in acute toxicity pattern.

EXAMPLES

The invention will now be illustrated by way of examples. The examples are by way of illustration only and in no way restrict the scope of the invention.

All the raw materials used in this example were of pharmaceutical grade. Equipments used were of conventional nature. Entire processing was done in an area with a controlled environment.

Example I

Two compositions were made with process runs A & B in this example. Process run B is comparative and not of the invention. Following ingredients were used in this example:

| | Ingredients | A | B |
|---|---|---|---|
| a) | Propofol | 1 g | 1 g |
| b) | 2-hydroxypropyl-β-cyclodextrin | 30 g | 20 g |
| c) | Glycerin | 2.25 g | 2.25 g |
| d) | Disodium edetate | 0.005 g | 0.005 g |
| e) | Water q.s. to | 100 ml | 100 ml |

Procedure:

2-hydroxypropyl-β-cyclodextrin was dissolved in 55 ml of Water at 25° C.–30° C. Propofol was added to HPBCD solution slowly under vigorous stirring at 25° C.–30° C. This solution was stirred at moderate speed for 3 hours maintaining the temperature at 25° C.–30° C.

Glycerin and 0.5 ml of Disodium edetate 1% w/v solution were added to the above solution under moderate stirring. The volume was made up to 100 ml with water. The clear solution obtained was filtered through 0.2μ filter, filled into glass vials under nitrogen, sealed and autoclaved.

While the composition A remained clear on autoclaving, composition B became turbid. This example shows that the ratio of propofol to HPBCD is important to give composition stable to autoclaving.

Propofol content of the composition was determined by HPLC method using 270 nm detector and a 4.6 mm×25 cm column containing packing L1. The flow rate was adjusted to 1.5 ml per minute. Mobile phase used consisted of water, acetonitrile and methanol in a volume ratio of 30:50:20.

The process run A giving composition having propofol content 10 mg/ml was repeated on a larger batch and used for stability studies, Results of stability studies are presented in Table I.

Example II

Two compositions were made with process runs C & D in this example. Process run D is comparative and not of the invention Following ingredients were used in this example:

| Ingredients | | C | D |
|---|---|---|---|
| a) | Propofol | 1 g | 1 g |
| b) | 2-hydroxypropyl-β-cyclodextrin | 30 g | 20 g |
| c) | Glycerin | 2.25 g | 2.25 g |
| d) | Disodium edetate | 0.005 g | 0.005 g |
| e) | Water q.s. to | 100 ml | 100 ml |
| f) | Dextrose solution 5% q.s. to | 500 ml | 500 ml |

Procedure:

Procedure followed was same as in Example I. However, after making up the volume to 100 ml with water it was further diluted to 500 ml with 5% Dextrose solution to bring propofol concentration to 2 mg/ml. It was then filtered through 0.2μ filter, filled into glass vials under nitrogen, sealed and autoclaved as per the procedure of Example I. While the composition (C) remained clear on autoclaving, composition (D) became turbid.

Propofol content of the composition was determined by the method specified under Example I.

The process run C giving composition having propofol content 2 mg/ml was repeated on a larger batch and used for stability studies. Results of stability studies are presented in Table I.

The composition of Example II (C) was used in animal studies and the results are presented in Table II.

Example III

Two compositions were made with process runs E & F in this example. Process run F is comparative and not of the invention. Following ingredients were used in this example:

| Ingredients | | E | F |
|---|---|---|---|
| a) | Propofol | 0.2 g | 0.2 g |
| b) | 2-hydroxypropyl-β-cyclodextrin | 6 g | 4 g |
| c) | Glycerin | 0.45 g | 0.45 g |
| d) | Disodium edetate | 0.001 g | 0.001 g |
| e) | Dextrose | 5 g | 5 g |
| f) | Water q.s. to | 100 ml | 100 ml |

Procedure:

2-hydroxypropyl-β-cyclodextrin was dissolved in 55 ml of Water at 25° C.–30° C. Propofol was added to HPBCD solution slowly under vigorous stirring at 25° C.–30° C.

This solution was stirred at moderate speed for 3 hours maintaining the temperature at 25° C.–30° C.

Glycerin and 0.1 ml of Disodium edetate 1% w/v solution were added to the above solution under moderate stirring. Dissolve dextrose in 20 ml of water and added to the above solution under moderate stirring. The volume was made up to 100 ml with water. The clear solution obtained was filtered through 0.2μ filter, filled into glass vials under nitrogen, sealed and autoclaved. While the composition E remained clear on autoclaving, composition F became turbid.

This example shows that the ratio of propofol to HPBCD is important to give composition stable to autoclaving.

Example IV

Following ingredients were used in this example:
a) Propofol 1 g
b) 2-hydroxypropyl-β-cyclodextrin 30 g
c) Glycerin 2.25 g
d) Disodium edetate 0.005 g
e) Absolute alcohol (Ethanol) 62 ml
f) Water q.s. to make 100 ml Procedure:

2-hydroxypropyl-β-cyclodextrin was dissolved in 60 ml of Ethanol at 25° C.–30° C. Propofol was dissolved in remaining quantity of Ethanol and added to HPBCD solution slowly under vigorous stirring at 25° C.–30° C. This solution was stirred at moderate speed for 15 minutes maintaining the temperature at 25° C.–30° C. This alcoholic solution was rotary evaporated under vacuum, at 40° C. to complete dryness.

The solid complex obtained was dissolved completely in 55 ml of water to obtain a clear aqueous solution.

Glycerin and 0.5 ml of disodium edetate 1% w/v solution were added to the above solution under moderate stirring. The volume was made up to 100 ml with water.

The clear solution obtained was filtered through 0.2μ filter, filled into glass vials under nitrogen, sealed and autoclaved.

This composition remained clear on autoclaving.

Example V

Following ingredients were used in this example:
a) Propofol 0.2 g
b) 2-hydroxypropyl-β-cyclodextrin 6 g
c) Absolute alcohol (Ethanol] 13 ml
d) Glycerin 0.45 g
e) Disodium edetate 0.001 g
f) Dextrose 5 g
g) Water q.s. to make 100 ml Procedure:

2-hydroxypropyl-β-cyclodextrin was dissolved in 12 ml of Ethanol at 25° C.–30° C. Propofol was dissolved in remaining quantity of Ethanol and added to HPBCD solution slowly under vigorous stirring at 25° C.–30° C. This solution was stirred at moderate speed for 15 minutes maintaining the temperature at 25° C.–30° C. This alcoholic solution was rotary evaporated under vacuum, at 40° C. to complete dryness.

The solid complex obtained was dissolved completely in 55 ml of water to obtain a clear aqueous solution.

Glycerin and 0.1 ml of disodium edetate 1% w/v solution were added to the above solution under moderate stirring.

The required quantity of Dextrose was dissolved in 30 ml of water. Dextrose solution was added to the above solution under moderate stirring and the volume was made up to 100 ml using water. The clear solution obtained was filtered through 0.2μ filter, filled into glass vials under nitrogen, sealed and autoclaved.

This composition remained clear on autoclaving.

Example VI

Three compositions were made with process runs G, H & I in this example. Process run H is comparative and not of the invention. Following ingredients were used in this example:

| Ingredients | G | H | I |
|---|---|---|---|
| a) Propofol | 1 g | 1 g | 1 g |
| b) 2-hydroxypropyl-β-cyclodextrin | 30 g | 20 g | 60 g |
| c) Water q.s. to | 100 ml | 100 ml | 100 ml |

Procedure:

2-hydroxypropyl-β-cyclodextrin was dissolved in 55 ml of Water at 25° C.–30° C. Propofol was added to HPBCD solution slowly under vigorous stirring at 25° C.–30° C. This solution was stirred at moderate speed for 3 hours maintaining the temperature at 25° C.–30° C. The volume was made up to 100 ml with water.

The clear solution obtained was filtered through 0.2μ filter, filled into glass vials under nitrogen, sealed and autoclaved.

While the composition G & I remained clear on autoclaving, composition H became turbid.

This example shows that the ratio of propofol to HPBCD is important to give composition stable to autoclaving.

Example VII

Following ingredients were used in this example:
a) Propofol 1 g
b) 2-hydroxypropyl-β-cyclodextrin 30 g
c) Potassium dihydrogen phosphate 0.476 g
d) Sodium hydroxide 0.028 g
e) Water q.s. to make 100 ml Procedure:

Buffer solution was prepared by dissolving Potassium dihydrogen phosphate and Sodium hydroxide in 55 ml of water.

2-hydroxypropyl-β-cyclodextrin was dissolved in the above buffer solution at 25° C.–30° C. Propofol was added to HPBCD solution slowly under vigorous stirring at 25° C.–30° C. This solution was stirred at moderate speed for 3 hours maintaining the temperature at 25° C.–30° C. The volume was made up to 100 ml with water.

The clear solution obtained was filtered through 0.2μ filter, filled into glass vials under nitrogen, sealed and autoclaved.

This composition remained clear on autoclaving.

Example VIII

Following ingredients were used in this example:
a) Propofol 1 g
b) 2-hyroxypropyl-β-cyclodextrin 30 g
c) Absolute alcohol (Ethanol) 60 ml
d) Water q.s. to make 100 ml Procedure:

2-hydroxypropyl-β-cyclodextrin was dissolved in 60 ml of Ethanol at 25° C.–30° C. Propofol was added to HPBCD solution slowly under vigorous stirring at 25° C.–30° C. This solution was stirred at moderate speed for 15 minutes maintaining the temperature at 25° C.–30° C. This alcoholic solution was rotary evaporated under vacuum, at 40° C. to complete dryness.

The solid complex obtained was dissolved completely in 55 ml of water to obtain a clear aqueous solution. The volume was made up to 100 ml with water.

The clear solution obtained was filtered through 0.2μ filter, filled into glass vials under nitrogen, sealed and autoclaved.

This composition remained clear on autoclaving.

Example IX

Following ingredients were used in this example:
a) Propofol 1 g
b) 2-hydroxypropyl-β-cyclodextrin 30 g
c) Absolute alcohol (Ethanol) 2 ml
d) Water q.s. to make 100 ml Procedure:

2-hydroxypropyl-β-cyclodextrin was dissolved in 55 ml of water at 25° C.–30° C.

Propofol was dissolved in 2 ml of ethanol and added to HPBCD solution slowly under vigorous sting at 25° C.–30° C. This solution was stirred at moderate speed for 60 minutes maintaining the temperature at 25° C.–30° C. This solution was rotary evaporated under vacuum, at 40° C. to remove alcohol completely. The volume was made up to 100 ml with water.

The clear solution obtained was filtered through 0.2μ filter, filled into glass vials under nitrogen, sealed and autoclaved.

This composition remained clear on autoclaving.

All the above mentioned Examples clearly indicate that complexation of propofol with 2-hydroxypropyl-β-cyclodextrin in 1:30 to 1:60 wt./wt. ratio makes the product stable to autoclaving.

TABLE I

STABILITY DATA FOR PROPOFOL CLEAR SOLUTION AT RECOMMENDED STORAGE TEMPERATURE OF 2° C.–8° C.

| | Example I-Sample A (Propofol content 10 mg/ml) | | Example II-Sample C (Propofol content 2 mg/ml) | |
|---|---|---|---|---|
| Duration ↓ | Physical observation | Assay | Physical observation | Assay |
| Initial | Clear colourless solution | 100.70% | Clear colourless solution | 101.60% |
| 6 Months | Clear colourless solution | 100.22% | Clear colourless solution | 99.80% |
| 12 Months | Clear colourless solution | 99.16% | Clear colourless solution | 99.52% |
| 18 Months | Clear colourless solution | 98.73% | Clear colourless solution | 98.65% |

TABLE II

COMPARATIVE STUDY OF PROPOFOL CLEAR SOLUTION (PCS)* WITH PROPOFOL EMULSION (PE) FOR ONSET AND DURATION OF ANAESTHESIA IN MICE BY INTRAPERITONEAL ROUTE

| | Dose | | | | | | | | | |
|---|---|---|---|---|---|---|---|---|---|---|
| | 10 mg/kg | | 20 mg/kg | | 40 mg/kg | | 80 mg/kg | | 120 mg/kg | |
| Type of Product | PE | PCS | PE | PCS | PE | PCS | PE | PCS | PE | PCS |
| Onset time in Min. | ** | 2.32 to 2.84 | ** | 0.73 to 1.93 | ** | 0.52 to 1.23 | 1.60 to 3.30 | 0.20 to 1.06 | 0.50 to 1.54 | 0.17 to 0.95 |
| Duration of anesthesia in min. | — | 0.013 to 0.053 | — | 5.39 to 6.47 | — | 14.33 to 18.73 | 10.18 to 17.08 | 13.58 to 47.36 | 52.54 to 59.74 | 41.29 to 43.87 |

*Example II sample C
**No onset of action
Propofol emulsion (PE) - Prepared as per prior art containing Soybean oil & Egg phosphatide.

The invention claimed is:

1. An autoclaved stable clear aqueous pharmaceutical composition of propofol, suitable for parenteral administration comprising propofol and 2-hydroxypropyl-B-cyclodextrin (HPBCD) in a wt. ratio of propofol: HPBCD from about 1:30 to about 1:60.

2. The autoclaved stable clear aqueous pharmaceutical composition of propofol, suitable for parenteral administration as claimed in claim 1 wherein the composition further comprises other conventional additives as required by parenteral dosage form.

3. The autoclaved stable clear aqueous pharmaceutical composition of propofol, suitable for parenteral administration as claimed in claim 1 wherein the content of propofol is from about 1 mg/ml to about 20 mg/ml.

4. The autoclaved stable clear aqueous pharmaceutical composition of propofol, suitable for parenteral administration as claimed in claim 1 wherein the content of propofol is about 10 mg/ml.

5. The autoclaved stable clear aqueous pharmaceutical composition of propofol, suitable for parenterai administration as claimed in claim 1 wherein the content of propofol is about 2 mg/ml.

6. The autoclaved stable clear aqueous pharmaceutical composition of propofol, suitable for parenteral administration as claimed in claim 1 wherein the wt./wt. ratio of propofol to HPBCD used is about 1:30.

7. The autoclaved stable clear aqueous pharmaceutical composition of propofol, suitable for parenteral administration as claimed in claim 2 wherein, said other conventional additives required by parenteral dosage form are selected from the group of pharmaceutically acceptable additives consisting of anticrystallising agents, antioxidants, buffers and isotonic diluents.

8. The autoclaved stable clear aqueous pharmaceutical composition of propofol, suitable for parenteral administration as claimed in claim 7 wherein, said additive is an anticrystallizing agents which is selected from the group of pharmaceutically acceptable compounds consisting of Glycerin, Polyethylene glycol, Propylene glycol or a mixture thereof.

9. The autoclaved stable clear aqueous pharmaceutical composition of propofol, suitable for parenteral administration as claimed in claim 7 wherein, said additive is an antioxidants which is selected from the group of pharmaceutically acceptable compounds consisting of Ethylene diamine tetraacetic acid and salts thereof, Sodium metabisulphite, Acetylcysteine, Ascorbic acid or a mixture thereof.

10. The autoclaved stable clear aqueous pharmaceutical composition of propofol, suitable for parenteral administration as claimed in claim 7 wherein, said additive is a buffer which is selected from the group of pharmaceutically acceptable buffers consisting of Phosphate buffers, Citrate buffers, Glycine buffers.

11. The autoclaved stable clear aqueous pharmaceutical composition of propofol, suitable for parenteral administration as claimed in claim 7 wherein, said additive is an isotonic diluent which is Dextrose solution or Sodium chloride solution.

12. A process for preparation of a stable autoclaved clear aqueous pharmaceutical composition of propofol, suitable for parenteral administration as claimed in claim 1, comprising steps of
    (i) addition of propofol as such or dissolved in a solvent to solution of 2-hydroxypropyl-B-cyclodextrin (HPBCD) either in water or other solvents in a wt. ratio of propofol : HPBCD from 1:30 to 1:60 under stirring;
    (ii) keeping the said solution of propofol and HPBCD under intimate contact till complexation of propofol with HPBCD is complete to obtain a clear bulk solution;
    (iii) removing said solvent if other than water, and adding water;
    (iv) making up the volume with water to the required concentration of propofol in said composition;
    (v) filtering the said composition obtained at the end of step (iv) through 2µ to 0.2µ filter;
    (vi) filling the said filtrate obtained at the end of step (v) in containers such as vials, ampoules, followed by nitrogen purging and sealing the filled containers;
    (vii) autoclaving the sealed containers filled with said filtrate.

13. The process, for preparation of a stable autoclaved clear aqueous pharmaceutical composition of propofol, suitable for parenteral administration as claimed in claim 12, further comprising addition of conventional additives as required by parenteral dosage form, before filtration step.

14. The process for preparation of a stable autoclaved clear aqueous pharmaceutical composition of propofol, suitable for parenteral administration as claimed in claim 12 wherein the content of propofol is from about 1 mg/ml to about 20 mg/ml.

15. The process for preparation of a stable autoclaved clear aqueous pharmaceutical composition of propofol, suitable for parenteral administration as claimed in claim 12 wherein, the content of propofol is about 10 mg/ml.

16. The process for preparation of a stable autoclaved clear aqueous pharmaceutical composition of propofol, suitable for parenteral administration as claimed in claim 12 wherein, the content of propofol is about 2 mg/ml.

17. The process for preparation of a stable autoclaved clear aqueous pharmaceutical composition of propofol, suitable for parenteral administration as claimed in claim 12 wherein the wt./wt. ratio of propofol to HPBCD used is about 1:30.

18. The process for preparation of a stable autoclaved clear aqueous pharmaceutical composition of propofol, suitable for parenteral administration as claimed in claim 12 wherein, propofol as such is added to HPBCD dissolved in water in step (i).

19. The process for preparation of a stable autoclaved clear aqueous pharmaceutical composition of propofol, suitable for parenteral administration as claimed in claim 12 wherein, propofol as such is added to HPBCD dissolved in water in step (i) and the intimate contact as per step (ii) is brought about by using High shear mixer, Colloid mill or High pressure homogeniser.

20. The process for preparation of a stable autoclaved clear aqueous pharmaceutical composition of propofol, suitable for parenteral administration as claimed in claim 12 wherein, for complexing with HPBCD, propofol dissolved in pharmaceutically acceptable organic solvents such as Ethanol, Methanol, Isopropyl alcohol or a mixture thereof is added to HPBCD solution in water in step (i).

21. The process for preparation of a stable autoclaved clear aqueous pharmaceutical composition of propofol, suitable for parenteral administration as claimed in claim 12 wherein, propofol solution in Ethanol is added to HPBCD solution in water in step (i).

22. The process for preparation of a stable autoclaved clear aqueous pharmaceutical composition of propofol, suitable for parenteral administration as claimed in claim 12 wherein, propofol as such is added to HPBCD dissolved in pharmaceutically acceptable organic solvents such as Ethanol, Methanol or a mixture thereof in step (i).

23. The process for preparation of a stable autoclaved clear aqueous pharmaceutical composition of propofol, suitable for parenteral administration as claimed in claim 12 wherein, propofol as such is added to HPBCD dissolved in Ethanol in step (i).

24. The process for preparation of a stable autoclaved clear aqueous pharmaceutical composition of propofol, suitable for parenteral administration as claimed in claim 12 wherein, for complexing with HPBCD, propofol dissolved in pharmaceutically acceptable organic solvents such as Ethanol, Methanol, Isopropyl alcohol or a mixture thereof is added to HPBCD solution in pharmaceutically acceptable organic solvents such as Ethanol, Methanol or a mixture thereof in step (i).

25. The process for preparation of a stable autoclaved clear aqueous pharmaceutical composition of propofol, suitable for parenteral administration as claimed in claim 12 wherein, propofol as solution in Ethanol is added to HPBCD solution in Ethanol in step (i).

26. The process for preparation of a stable autoclaved clear aqueous pharmaceutical composition of propofol, suitable for parenteral administration as claimed in claim 12 wherein, additives required by parenteral dosage form are selected from a group of pharmaceutically acceptable additives such as antioxidants, anticrystallising agents, buffers and isotonic diluents.

27. The process for preparation of a stable autoclaved clear aqueous pharmaceutical composition of propofol, suitable for parenteral administration as claimed in claim 26 wherein, anticrystallising agents are selected from a group of pharmaceutically acceptable compounds such as glycerin, Polyethylene glycol, Propylene glycol or a mixture thereof.

28. The process for preparation of a stable autoclaved clear aqueous pharmaceutical composition of propofol, suitable for parenteral administration as claimed in claim 26 wherein, said additive is an antioxidante which is selected from a group of pharmaceutically acceptable compounds such as Ethylene diamine tetraacetic acid and salts thereof, Sodium metabisulphite, Acetylcysteine, Ascorbic acid or a mixture thereof.

29. The process for preparation of a stable autoclaved clear aqueous pharmaceutical composition of propofol, suitable for parenteral administration as claimed in claim 26 wherein, said additive is a buffer which is selected from a group of pharmaceutically acceptable buffers such as Phosphate buffers, Citrate buffers, Glycine buffers.

30. The process for preparation of a stable autoclaved clear aqueous pharmaceutical composition of propofol, suitable for parenteral administration as claimed in claim 26 wherein, said additive is an isotonic diluent which is Dextrose solution or Sodium chloride solution.

* * * * *